United States Patent [19]
Vaillancourt

[11] Patent Number: 5,591,138
[45] Date of Patent: Jan. 7, 1997

[54] PROTECTED NEEDLE ASSEMBLY

[76] Inventor: Vincent L. Vaillancourt, 14 Runyon Dr., Livingston, N.J. 07039

[21] Appl. No.: 513,538

[22] Filed: Aug. 10, 1995

[51] Int. Cl.[6] .................................................. A61M 5/32
[52] U.S. Cl. .......................... 604/263; 604/192; 604/198
[58] Field of Search ................................... 604/263, 198, 604/192, 187, 110

[56] References Cited

U.S. PATENT DOCUMENTS

| | | | |
|---|---|---|---|
| 3,134,380 | 5/1964 | Armao | 604/198 |
| 3,354,881 | 11/1967 | Bloch | 604/198 |
| 4,775,369 | 10/1988 | Schwartz | 604/198 |
| 4,892,107 | 1/1990 | Haber | 604/198 |
| 4,894,055 | 1/1990 | Sudnak | 604/263 |
| 4,911,693 | 3/1990 | Paris | 604/198 |
| 4,923,447 | 5/1990 | Morgan | 604/198 |
| 4,932,940 | 6/1990 | Walker et al. | 604/198 |
| 5,015,242 | 5/1991 | Heifetz | 604/198 |
| 5,088,986 | 2/1992 | Nusbaum | 604/198 |
| 5,104,382 | 4/1992 | Brinkerhoff | 604/165 |
| 5,106,379 | 4/1992 | Leap | 604/198 |
| 5,207,646 | 5/1993 | Brunel | 604/110 |
| 5,209,739 | 5/1993 | Talalay | 604/198 |
| 5,242,401 | 9/1993 | Colsky | 604/198 |
| 5,267,972 | 12/1993 | Anderson | 604/192 |
| 5,290,254 | 3/1994 | Vaillancourt | 604/198 X |
| 5,292,314 | 9/1994 | D'Alessio et al. | |

*Primary Examiner*—John D. Yasko
*Attorney, Agent, or Firm*—McAulay Fisher Nissen Goldberg & Kiel, LLP

[57] ABSTRACT

The protected needle assembly is provided with various enhancements for improved use. In one embodiment, a V-shaped slot is provided at the rear of the guide slot so that the retractable sheath can be locked in a retracted position. In another embodiment, a cam surface is provided at the front of the guide slot to direct the projection on the sheath into a position to lock of the sheath in an extended position. An additional inclined guide portion may be provided at the forward end of the guide slot for intramuscular injection use. The movable sheath may also be mounted on a syringe without need for a resilient bias or may incorporate a coiled spring or rubber strip to bias the sheath into an extended position. Another embodiment allows for multiple or universal use of the needle assembly.

19 Claims, 4 Drawing Sheets

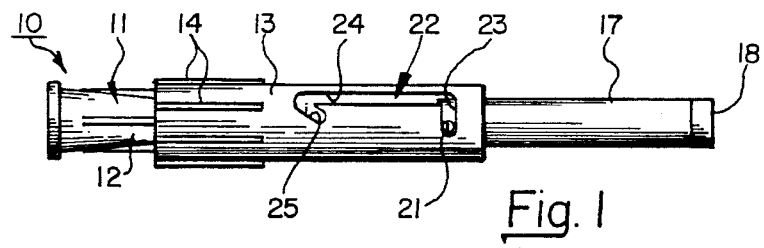
Fig. 1
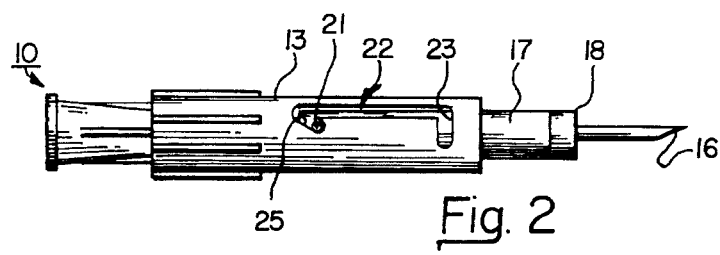
Fig. 2
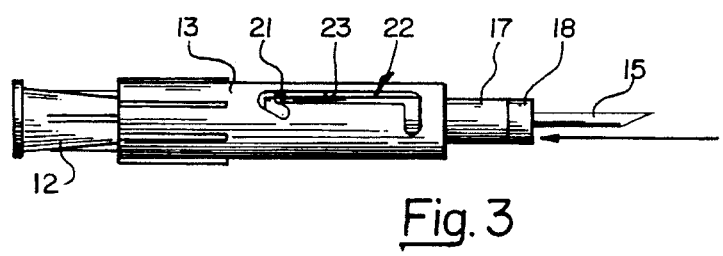
Fig. 3
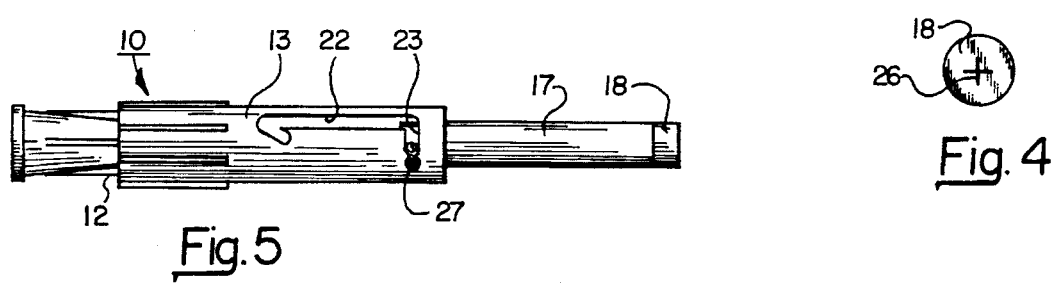
Fig. 5
Fig. 4
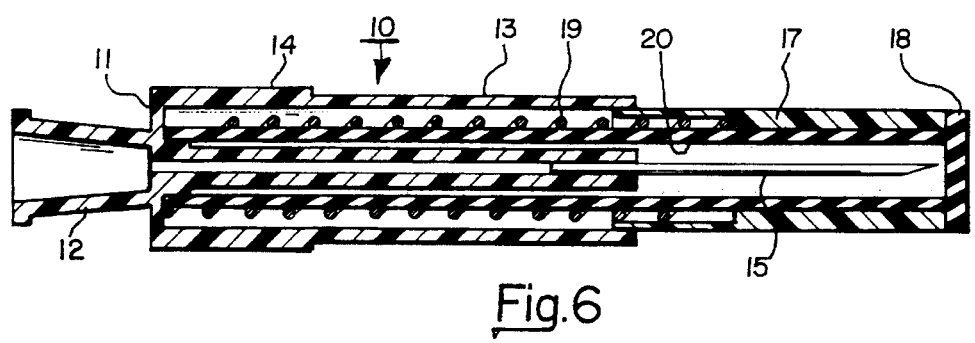
Fig. 6

PROTECTED NEEDLE ASSEMBLY

This invention relates to an improved protected needle assembly. More particularly, this invention relates to a needle assembly constructed in a manner to prevent needle sticks.

As is known, one major problem with a hypodermic needle as well as other needles is the threat of cutting oneself or another thereby exposing a blood vessel to the environment. This has become especially important in a hospital atmosphere where AIDS patients or AIDS members of a staff can infect others by having their blood interact, for example, by touching another person.

Various techniques have been proposed to overcome this problem. For example, in some cases, use has been made of a shield or cap which is placed over a needle after use. Generally, this is intended to allow only a one-time use of the needle with an automatic covering system which prevents further use. However, during actual use of such a needle, the needle does not remain totally protected. Further, if the needle is re-used, there is no provision to sheath the needle.

U.S. Pat. No. 4,629,453 describes a protection device for a hypodermic needle which uses a protective cap which can be fitted over a needle when the needle is not in use.

U.S. Pat. No. 4,735,618 describes a protective enclosure for hypodermic needles which employs a cap-like needle guard which is positioned about a free end of a needle while being connected via collapsible arms to a tubular sleeve mounted about a needle housing. When in use, the cap is pressed against a patient under a sufficient force to cause collapsing of the collapsible arms so that the cap slides back over the needle. However, when not intended for use, any accidental pushing in on the cap by a user can cause an inadvertent needle stick.

U.S. Pat. No. 3,134,380 describes a shielded hypodermic needle wherein a needle is sheathed within a collapsible tube so that upon collapsing of the tube, the needle is exposed. In addition, a spring is provided within the tube so as to return the collapsed tube to an extended state.

U.S. Pat. No. 4,725,267 describes the use of a resilient collapsible sheath which can be mounted over a needle to contain the needle when not in use.

U.S. Pat. No. 4,695,274 describes a removable needle attachment consisting of a needle-holding member and a safety jacket. As described, the jacket is provided with a slot which receives a guide tab of the needle-holding member so as to prevent sliding of the safety jacket back and forth on the needle holding member in order to permit piercing of the needle through a wall of the safety jacket. However, in such a construction, as in other similar constructions, a risk of inadvertent needle sticking occurs should the guide tab be disposed in an unlocking condition within the slot.

A protective needle assembly is described in U.S. Pat. No. 5,472,430 which overcomes many of the problems of the previously known structures. The following description is directed to improvements on the structure described in the co-pending patent application.

It is an object of the invention to provide an improved locking arrangement for a protective sheath for shielding a hypodermic needle which is relatively fool proof.

It is another object of the invention to provide a needle assembly with a protective sheath with a simple arrangement for biasing the sheath into an extended locked position.

It is another object of the invention to improve the construction of a protected needle assembly for various uses.

It is another of the invention to provide for a secure locking of a sheath in an extended protecting position after use for disposal purposes.

It is another object of the invention to employ a protected needle assembly on a syringe.

Briefly, the invention is directed to a protected needle assembly, such as described in the copending application, which is comprised of a housing including a rigid tube, a needle mounted in the housing and extending through and beyond the tube for percutaneous insertion into a patient and a retractable sheath which is disposed about the needle with one end extending beyond the needle in protective relation. The sheath is movable longitudinally of the rigid tube and needle between an extended position covering over the needle and a retracted position exposing the needle. In addition, at least one projection is provided on the sheath or the tube while a guide slot is provided on the other of the sheath and the tube for receiving the projection. Further, the guide slot has a circumferentially directed portion for receiving the projection in the extended position of the sheath and a longitudinally directed portion for receiving the projection during movement of the sheath to the retracted position. A resilient means is also provided for biasing the sheath from the retracted position to the extended position.

In accordance with the invention, various improvements are provided for this type of protected needle assembly.

More specifically, the guide slot is formed with an inclined portion which is disposed at an opposite end from and which is directed toward the end of the slot at which the circumferentially directed portion is located. This inclined portion defines a V-shape or the like with the longitudinally directed portion of the slot so as to receive and retain the projection when the sheath has been moved into the retracted position. In this embodiment, with the sheath in the extended needle-protecting position, the protected needle assembly is placed against a septum to be pierced. For example, the septum may be a rubber septum of a connector, a septum on a container or the skin of a patient. In any event, after the needle assembly has been abutted against the septum, a slight amount of pressure is applied to obtain a friction surface between the septum and the face of the sheath. A slight twist is then imparted to the assembly by the user to position the projection, i.e. safety pin, out of the circumferentially directed portion of the guide slot and in line with the longitudinally directed portion of the guide slot. The user then pushes forward to have the needle of the assembly penetrate into the septum as well as through any septum on the end of the sheath, depending upon the construction of the needle assembly. When the projection moves to the end of the longitudinally directed portion of the guide slot, the user imparts another slight twist so that the projection moves into the inclined portion of the guide slot. At this time, the resilient biasing means moves the projection forwardly into the inclined portion of the slot so as to lock the sheath in place with the needle in the pierced septum. Alternatively, where the resilient biasing means itself is distorted by the initial twisting of the assembly, a residual bias is imparted to the biasing means which is sufficient to turn the sheath so that the projection moves into the inclined portion of the V-shaped slot.

In order to remove the needle from the septum, pressure is applied to the needle assembly to push the sheath against the septum and the needle farther into the septum. This causes the projection to move out of the inclined portion of the guide slot back into alignment with the longitudinally directed portion of the guide slot. When pressure is released and the needle assembly pulled from the pierced septum, the resilient biasing means causes the sheath to move from the retracted position into the extended position to again move over the needle. When the projection reaches the end of the longitudinally directed portion of the guide slot, the bias introduced during manufacture causes the projection to again move into the circumferentially directed portion of the guide slot to secure the sheath in the extended position.

The inclined portion of the guide slot may, alternatively, be directed circumferentially in the same manner as the circumferentially directed portion at the forward end of the guide slot. However, having this portion of the guide slot inclined ensures a locking fit.

In another embodiment, the circumferentially directed portion of the guide slot may be provided with a cam-shaped surface for directing the projection from the longitudinally directed portion circumferentially into the circumferentially directed portion when the sheath is biased into the extended position. In this embodiment, it is not necessary to build in an initial bias in the needle assembly in order to move the projection into the circumferentially directed guide slot portion.

In still another embodiment, the guide slot is provided with an inclined portion extending from the longitudinally directed portion opposite to and at the same end as the circumferentially directed portion in order to receive the projection prior to movement of the projection relative to and along the longitudinally directed portion. This embodiment is particularly favorable for intramuscular injections. That is to say, in intramuscular injections, there is a need for the needle to be protected by the sheath just prior to injection while being free to move in the longitudinal direction of the needle axis at injection.

In still another embodiment, a constricted portion is disposed adjacent the end of the circumferentially directed guide slot portion for receiving the projection in a permanently locked relation for disposal purposes. That is, in this embodiment, after a needle assembly has been used and is ready to be discarded, the sheath is biased into the extended position and the projection is moved into the circumferentially directed portion of the slot. At this time, the user imparts a slight twist to the sheath while holding the housing so that the projection moves into the constricted portion adjacent to the guide slot thereby locking the projection in place. The degree of constraint or constriction is such that the projection cannot be readily removed from the constricted portion. In this sense, the sheath is locked in place in the extended position for disposal purposes.

In still another embodiment where the sheath is telescopically mounted over the tube, a stop is mounted on the tube for arresting movement of the sheath along the tube into a predetermined retracted position. In this embodiment, the stop may be movable into a desired position on the tube so as to adjust the depth of penetration of the needle into a septum, for example into a patient. As an alternative construction, the guide slot may be provided with one or more angularly disposed portions positioned intermediately of the longitudinally disposed portion of the guide slot in order to receive the projection and to thereby limit the length of exposure of the needle from the sheath.

In still another embodiment, the protected needle assembly is comprised, in part, of a syringe having a barrel, a plunger slidably mounted in the barrel and a needle extending from the barrel. In addition, the protected needle assembly includes a sheath which is disposed concentrically about the barrel with one end extending beyond the needle in protective relation. The sheath is movable longitudinally of the needle and the barrel between an extended position covering over the needle and a retracted position exposing the needle. As above, at least one projection is provided on one of the sheath and the barrel while a guide slot is provided in the other of the sheath and barrel to receive the projection. The guide slot is constructed as described in the copending application or as described above. In addition, a resilient means is provided for biasing the sheath from the retracted position to the extended position.

In this embodiment, the resilient means may be in the form of a rubber strip which is secured at each end to diametrically disposed parts of the sheath while a centrally disposed portion is provided with an aperture which fits over the needle and through which the needle passes. When the sheath is moved to the retracted position, the rubber strip elongates thereby having a biasing force developed therein for returning the sheath to the extended position.

In a further modified construction, a retainer ring is secured to the barrel of the syringe and has the projection projecting therefrom into the guide slot in the sheath. Thus, the retainer ring can be mounted over a conventional syringe in a retro-fit manner along with the sheath and resilient biasing means.

In a still further alternative construction, the syringe may have a needle separately mounted on the barrel, for example via a hub which is removably mounted on a tip of the syringe barrel. In this case, a retainer ring is provided for mounting on the needle hub and carries the projection which fits into the guide slot of the sheath.

In still another embodiment, the resilient means may be in the form of a coiled spring which is disposed within the sheath while being abutted at one end against the barrel of the syringe.

These and other objects and advantages of the invention will become more apparent from the following detailed description taken in conjunction with the accompanying drawings wherein:

FIG. 1 illustrates a side view of a protected needle assembly having an inclined slot portion at the rear end of the guide slot in accordance with the invention;

FIG. 2 illustrates a view similar to FIG. 1 of the protected needle assembly with the sheath in a retracted position;

FIG. 3 illustrates a view similar to FIGS. 1 and 2 during movement of the sheath into the retracted position in accordance with the invention;

FIG. 4 illustrates an end view of a septum at the end of the sheath having a slit valve therein in accordance with the invention;

FIG. 5 illustrates a view similar to FIG. 1 needle assembly having a constricted portion adjacent the guide slot for locking the sheath in a permanent manner in accordance with the invention;

FIG. 6 illustrates a cross-sectional view of the needle assembly of FIG. 1;

Figure 7:
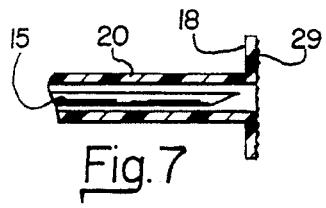
FIG. 7 illustrates a part cross-sectional view of a protective sheath having a roughened surface on a distal end for frictionally engaging a surface to be pierced in accordance with the invention.

Referring to FIG. 1, the protected needle assembly 10 is constructed in a manner similar to that as described in U.S. Pat. No. 5,472,430 filed Aug. 18, 1994 and that disclosure is incorporated by reference herein.

As illustrated in FIGS. 1 and 6, the protected needle assembly 10 comprises a housing 11 which includes a hub 12 at a proximal end for mounting on a suitable structure such as a drug delivery system, a syringe, a blood receiving receptacle and the like. In addition, the housing 11 has a rigid tube 13 of cylindrical shape having external ribs 14 mounted thereon to enhance manual grasping of the assembly 10.

As shown in FIG. 6, the hub 12 mounts a needle 15 having a sharp end 16 concentrically within the tube 13.

The assembly 10 also includes a sheath 17 which is telescopically mounted within the tube 13 and disposed concentrically about the needle 15 with one end extending beyond the needle 15 in protective relation. The sheath 17 is made of a rigid plastic material and has a septum 18, for example of rubber, mounted at the end of the sheath 17 to seal the needle 15 within the sheath 17. The sheath 17 is movable longitudinally of the needle 15 and tube 13 between an extended position as shown in FIG. 1 covering over the needle 15 and a retracted position as shown in FIG. 2 exposing the needle 15.

Referring to FIG. 6, a resilient means in the form of a coil spring 19 is provided within the rigid tube 13 so as to bias the sheath 17 from the retracted position to the extended position. As indicated, the spring 19 abuts the sheath 17 at one end and the housing 11 at the opposite end. In addition, the septum 18 is integral with a sleeve 20 which is secured to and within the sheath 17 and extends to a proximal end which abuts the housing 11. As indicated, the sleeve 20 is disposed within the spring 19. This sleeve 20 is made of the same material as the septum, for example, of rubber and allows the sheath 17 to be twisted relative to the housing tubing 13 so as to impart a bias on the sheath 17 in the circumferential direction. The sleeve 20 is also collapsible to allow the needle 15 to pierce the septum 18.

As shown in FIG. 1, the assembly 10 includes at least one projection 21 on the sheath 17 which is received within a guide slot 22 in the rigid tube 13. This guide slot 22 includes a circumferentially directed portion 23 at the forward end for receiving the projection 21 in the extended position of the sheath 17, a longitudinally directed portion 24 and an inclined portion 25 at the proximal end which is directed toward the forward end in order to receive and retain the projection 21 in the retracted position of the sheath 17 as indicated in FIG. 2. The inclined slot portion 25 forms a V-shaped slot with the longitudinally directed portion 24.

When the projection 21 on the sheath 17 is within the circumferential portion 23 of the slot of the tube 13, the sheath 17 cannot be moved from the extended position shown in FIG. 1. Thus, in order to use the needle assembly 10, the face of the septum 18 is brought against the skin of a patient or other suitable septum. At this time, the tube 13 is rotated slightly so as to align the projection 21 with the longitudinally disposed portion 24 of the guide slot 22.

Continued pressure on the housing 11 causes the tube 13 to slide telescopically forwardly along the sheath 17 with the projection 21 sliding within the longitudinally disposed portion 24 of the guide slot 22 as indicated in FIG. 3. At the same time, the needle 15 pierces through the septum 18 into the patient or through a septum, as the case may be. When the projection 21 reaches the end of the longitudinal portion 24 of the guide slot and pressure on the assembly 10 is released, the residual stress in the rubber sleeve 20 causes the sheath 17 to rotate within the tube 13 so that the projection 21 moves into the inclined portion 25 of the guide slot thereby locking the sheath 17 in the retracted position shown in FIG. 2.

The sheath 17 may be locked in the retracted position shown in FIG. 2 when the needle assembly 10 is to remain in a patient or other septum. Thus, the bias of the spring 19 and the bias of the collapsible sleeve 20 are prevented from biasing the needle 15 out of the patient inadvertently. In addition, the needle assembly 10 may be taped to the patient or otherwise secured in place.

Referring to FIG. 4, the rubber septum 18 may be provided with a slit valve for certain uses. For example, when a parenteral vial or other drugstore container is ingressed (pierced) for purposes of transferring a drug (or other medication) from the container to a syringe which is connected to the proximal end of the protected needle assembly 10, there normally exists a requirement that the user be able to dispense a small quantity of drug into a sink, waste basket, and the like prior to administration. In this manner, the exact quantity to be dispensed now remains in the syringe and the user may dispense the entire quantity without regard to measuring out the dose during administration which of itself is a very difficult task. Having the slit valve in the septum 18 allows the user to push out the undesired amount of medication. In this regard, a slit of 0.045 inches has been found to be adequate to perform this operation without compromising product sterile integrity. In those cases where the users are to fill the syringe with air contained in a sterile environment, for example, a hospital pharmacy clean room, there may be a need for a two-way valve.

Of note, any valve type design which will open on the development of approximately 5 or more pounds of negative pressure will allow for air to be ingested into the syringe and still maintain a sterile barrier. The simplest means for accomplishing this requirement is to provide a Y or cross-slit valve 26 as illustrated in FIG. 4. These types of valves will allow for both air ingestion and dispensing of medication while the needle 15 remains sheathed.

Referring to FIG. 5, wherein like reference characters indicate like parts as above, a constricted portion 27 is disposed adjacent the end of the circumferentially directed portion 23 of the guide slot for receiving the projection 21 in a permanently locked relation for disposal purposes. In this respect, the constricted portion 27 is sized so that the projection 21 can be manually pushed therein by twisting of the sheath 17 relative to the tube 13. The constricted portion 27 is sized so that the projection 21 cannot be moved out of the constricted portion 27 back into the circumferential portion 23 of the guide slot. This provides a "final" positive locking feature which allows the user to be assured that the needle 15 not be exposed so as to place a user at risk of being cut. At the same time, the positive locking feature allows the needle assembly 10 to be discarded in a way that does not require excessive cost.

As also shown in FIG. 5, the sheath 17 may be provided with an air filter 28 to permit filtered air to enter into the sheath 17. In those cases where there is no need for a slit in the septum 18, for one reason or another, or where the user wishes to ingest air which is not contamination-free, then the air filter 28 allows air to enter into a syringe or whatever else may be attached to the proximal end of the needle assembly 10 without compromising sterility of the system.

Figure 8:
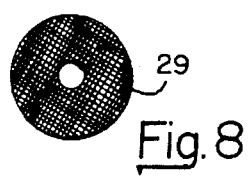
FIG. 8 illustrates a front view of the roughened surface of the sheath of FIG. 7.

Referring to FIGS. 7 and 8, wherein like reference characters indicate like parts as above, the septum 18 or the sheath 17 where a septum 18 is not used, is provided with a surface on the distal end for frictionally engaging a surface to be pierced. In this case, it is important that the surface which interfaces with the septum to be pierced has a sufficient friction resistance property to readily engage the septum to be pierced and not slip relative to the septum upon the application of a slight pressure which is sufficient to overcome the bias of the resilient means. In this respect, materials such as silicone rubber, natural rubber, latex free rubber and thermoplastic elastomeric materials satisfy this requirement. Also, a thermoplastic material which has a roughened surface 29, such as an abraded, striated or irregular pattern, is suitable. Also soft materials, such as a semi-rigid or flexible PVC should provide adequate frictional properties.

Figure 9:
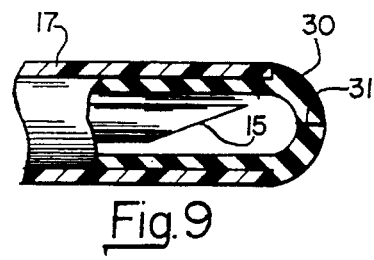
FIG. 9 illustrates a cross-sectional view of a cap which is mounted at the end of the protective sheath with the cap having a hemispherical tip in accordance with the invention.

Referring to FIG. 9, the sleeve 20 may be provided with a cap 30 of hemispherical shape to facilitate use of the assembly, for example, for anesthetizing a patient locally in an area, such as the fingers, where a normal profile is almost impossible to achieve. In this case, the cap 30 is made of rubber or the like so as to be readily collapsible while presenting a high profile. As above, the cap 30 is fitted into the rigid tube 13 and may be provided with a slit 31.

Figure 10:
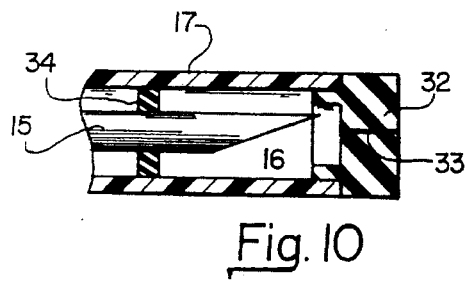
FIG. 10 illustrates a cross-sectional view of a sheath having a cap mounted on one end with a washer internally of the sheath in accordance with the invention.

Referring to FIG. 10, in another embodiment, the sheath 17 is provided with a cap 32 for sealing the needle 15 in place. As above, the cap 32 is provided with a slit 33 to facilitate passage of the needle 15. This cap 32 is secured to and within the end of the sheath 17 in any suitable permanent manner. In addition, a washer 34 is sealingly mounted in the sheath 17 and slidably receives the needle 15. As indicated, the washer 34 is disposed near a distal end of the needle 15. The washer 34 is used to isolate that portion of the needle 15 which will be used to ingress the septum/patient. This assures that the needle 15 is clean prior to use.

Figure 11:
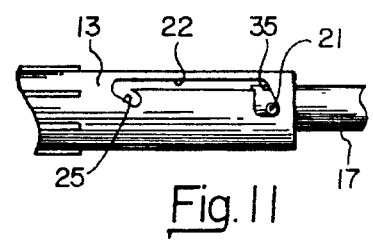
FIG. 11 illustrates a partial view of a guide slot employing a cam-shaped surface for directing the projection into the circumferentially directed guide slot portion in accordance with the invention.

For most injections into a patient through the skin, it is usually necessary to be able to see the bevel i.e. tip 16, of the needle 15 and to align the bevel properly, for example, generally in an "up" position. In order to accomplish this, the sheath 17 is made of a suitable material which is clear. For example, plastics which meet this requirement include polycarbonates, acrylics, polypropylene and polyethylene terephthalate. In addition, the cap 32 is made of a silicone rubber which provides both a sterile connection and clarity, Referring to FIG. 11, wherein like reference characters indicate like parts as above, the circumferentially directed portion 23 of the guide slot 22 is provided with a cam-shape surface 35 for directing the projection 21 from the longitudinally directed portion 24 of the guide slot circumferentially into the circumferentially directed portion 23 when the sheath 17 is biased into the extended position. In this embodiment, it is not necessary to build in an initial bias in order to move the projection 21 from the longitudinal portion 24 of the guide slot into the circumferential portion 23 of the guide slot. In this case, upon extension of the sheath 17, the projection 21 follows the path of the somewhat curved cam-shaped surface 35 and automatically locks the sheath 17 in place with the needle (not shown) in the protected position. There is no need to bias the spring 19 or rubber sleeve 20 (see FIG. 6). Instead, the axial force imparted by the springs/rubber sleeve combination is sufficient to force the projection 21 to follow the cam-shaped surface as the projection 21 reaches that part of the guide slot. When a subsequent axial force is imposed on the needle assembly, the projection 21 simply abuts the wall of the circumferentially disposed portion 23 so that the sheath 17 is prevented from retracting to the retracted position.

Figure 12:
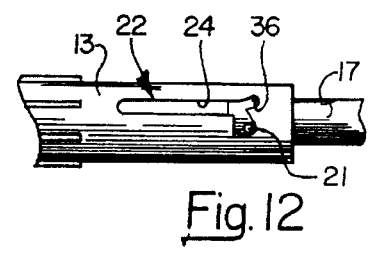
FIG. 12 illustrates a view of a needle assembly employing an inclined slot portion opposite the circumferentially directed portion to receive the projection prior to movement of the sheath to the retracted position in accordance with the invention.

Referring to FIG. 12, the guide slot may also be provided with an inclined portion 36 at the same end as the circumferentially directed portion 23. As indicated, the inclined portion 36 is opposite to the circumferentially directed portion 23 in order to receive the projection 21 prior to movement of the projection 21 relative to and along the longitudinally directed portion 24 of the guide slot. This embodiment is particularly useful for intramuscular injections. In this respect, for intramuscular injections, there is usually a need for the needle 15 to be protected by the sheath 17 just prior to injection while being free to move longitudinally. The inclined portion 36 allows the user to manually move the projection 21 over to this alternative location just prior to injection.

Upon injection, the Dart method is used. This method is similar to throwing darts in that the needle with an attached syringe is held like a dart and upon locating an appropriate muscle tissue location, the needle is jabbed into the skin. At this time, the sheath 17 readily moves with no further manipulation exposing the needle 15 to muscular tissue. Since the muscles provide substantial resistance, there is no need for an inclined slot portion at the rear as in FIG. 1 in order to hold the sheath 17 in place. Upon withdrawal from the patient, the sheath 17 automatically retracts thereby resheathing the needle 15 and the projection 21 moves into the safety position locking the sheath 17 and rendering the needle protected.

In an alternative procedure, just prior to needle insertion, the sheath 17 is unlocked and moved to the retracted position, for example, into the V-shaped slot as indicated in FIG. 2 thereby exposing the needle 15 and locking the sheath 17 in the retracted position. Upon needle insertion (jabbing), the needle 15 passes into the muscular tissue until being stopped by the distal end of the sheath 17 which receives pressure from the tissue. This pressure automatically unlocks the sheath 17 from the V-shaped slot. Upon retraction of the needle from a muscular tissue, the needle is automatically resheathed by the sheath 17. The advantage of this technique is that it conforms more nearly to existing nursing procedures and allows a nurse to totally visualize the needle prior to insertion. However, there is an element of potential risk to the nurse since the needle 15 is exposed. In either case, the nurse may see the needle through the clear plastic sheath 17 and position the bevel of the needle 15 "up" prior to the insertion.

Figure 13:
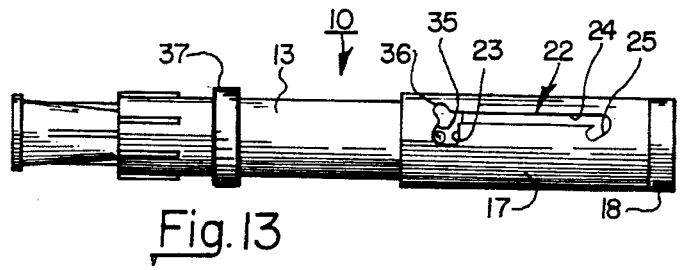
FIG. 13 illustrates a side view of a modified protected needle assembly employing a movably mounted stop for arresting movement of the sheath to a retracted position in accordance with the invention.

Referring to FIG. 13, wherein like reference characters indicate like parts as above, the sheath 17 may be telescopically mounted over the tube 13. In this case, a stop in the form of a washer 37 is movably mounted on the tube 13 for arresting movement of the sheath 17 along the tube 13 into a predetermined retracted position. This embodiment is especially useful for intramuscular injections where there is a need for a nurse to preset the exposed portion of the needle to the desired depth. In this respect, the tube 13 may be premarked to indicate the depths of penetration of the needle. In this case, the stop 37 may be used to indicate the maximum depth of penetration. Alternatively, as shown in FIG. 14, the guide slot 22 may be provided with a plurality of angularly disposed portions 38 along the longitudinal portion 24 to receive the projection 21 therein in order to limit the length of exposure of the needle from the sheath 17.

Depending upon the structure to which the needle assembly 10 is connected at the proximal end, the needle assembly may be used for injecting a medicament into a muscle of a patient. In this regard, the washer 37 has moved along the tube 13 into a predetermined position relative to the sheath 17 to indicate the desired depth of penetration for the needle (not shown) into the muscle of a patient. Thereafter, the needle assembly 10 is directed against the patient to cause the sheath 17 to retract along the tube 13 up to the stop washer 37 while the needle penetrates through the septum 18 into the muscle of a patient. During this time, the sheath moves against the bias of the spring (not shown). Hence, when the needle is pulled from the muscle of the patient, the spring automatically returns the sheath 17 to the extended position as illustrated in FIG. 13.

Figure 14:
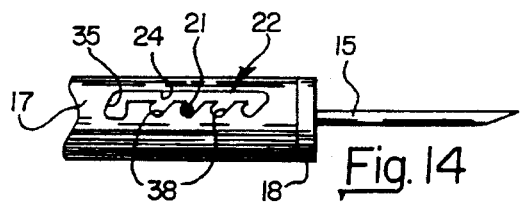
FIG. 14 illustrates a part view of a guide slot having angularly disposed portions for arresting movement of the sheath in accordance with the invention.
Figure 18:
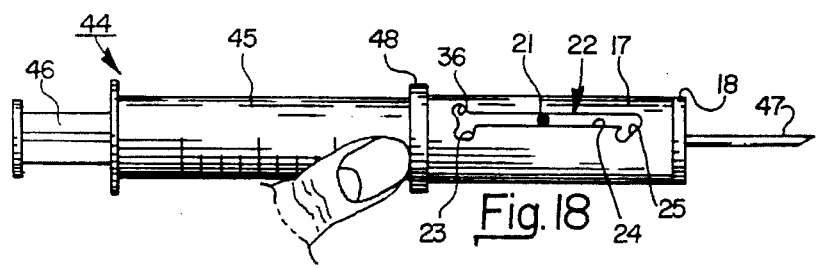
FIG. 18 illustrates a side view of a syringe having a protective sheath mounted thereon in accordance with the invention.

The embodiment illustrated in FIG. 14 may be used in a different manner. In this case, the sheath 17 is retracted against the biasing force of the spring along the barrel (not shown) to a predetermined locked position relative to the barrel in order to expose a predetermined length of the needle 15 through the septum 18. As illustrated, the projection 21 is located at the middle-most angularly disposed portion 38 so as to lock the sheath 17 relative to the barrel (not shown). At this time, the nurse or other user is able to determine the depth of penetration to which the needle 15 will be subjected in the muscle of a patient.

Where the sheath 17 is mounted on a syringe, for example, a syringe 44 as illustrated in FIG. 18 having a barrel 45 for containing a medicament, a needle 15 projecting from the barrel 45 to conduct the medicament therethrough, and a plunger 46 slidably mounted in the barrel 45. In this case, the sheath 17 is telescopically mounted on the barrel 45 concentrically of the needle 15.

Thereafter, the syringe is directed against the patient to cause the exposed needle to penetrate into the muscle of the patient up to the sheath 17 abutting the patient. At this time, the syringe plunger 46 would be depressed into the barrel 45 in order to inject medicament into the muscle of the patient.

At the time that the sheath 17 abuts against the patient, the sheath is further retracted a slight distance relative to the barrel 45 so that the projection 21 is moved into the longitudinal portion 24 of the guide slot 22 thereby unlocking the sheath 17 relative to the barrel 45. Thereafter, the needle 15 is withdrawn from the patient while the sheath 17 is automatically moved into the extended position under the biasing force of the spring (not shown) between the sheath 17 and the barrel 45 of the syringe.

Figure 15:
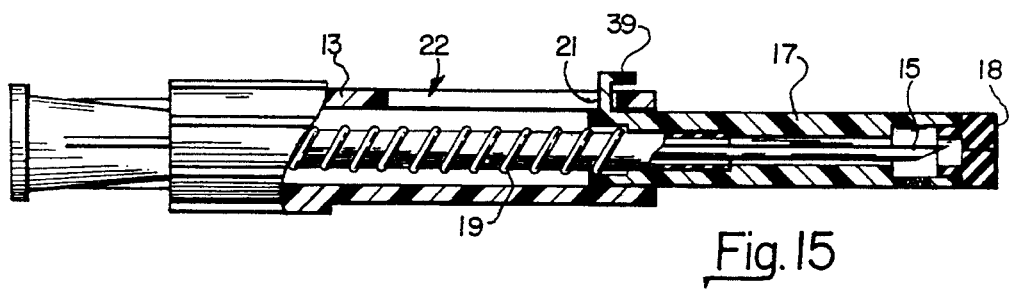
FIG. 15 illustrates a part cross-sectional view of a protected needle assembly having a manually engagable portion on the projection extending from the guide slot.

Referring to FIG. 15, wherein like reference characters indicate like parts as above, the projection 21 may be provided with a manually engagable portion 39 which extends radially outwardly of the tube 13. This manually engagable proportion 39 may be enlarged to provide a profile which can be manually grasped. This embodiment is particularly useful for occasions in which the user may wish to control the movements of the sheath 17 and for specialized uses of the needle 15. This may include oncology and neonatology uses. By using such an engagable portion (or detent), the user can control the sequence and movements of the protected needle assembly to his/her particular requirements.

Figure 16:
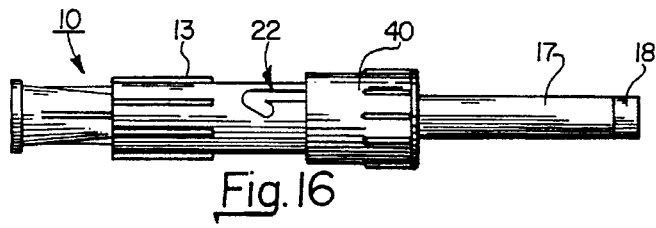
FIG. 16 illustrates a side view of a protected needle assembly employing a connector for connecting the needle assembly to another member in accordance with the invention.
Figure 17:
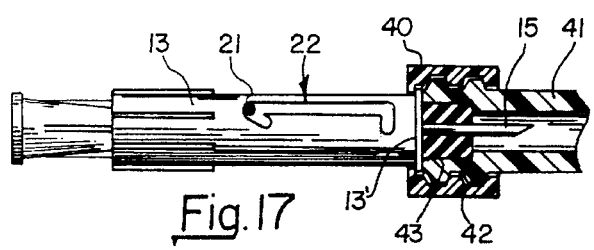
FIG. 17 illustrates a part cross-sectional view of the needle assembly of FIG. 16 coupled to another member via the connector.

Referring to FIGS. 16 and 17, in a number of uses, especially where the needle will be used as a portion of a line set, for example connecting one line with a second line and maintaining that connection, there is a need for alternative methods other than taping to secure the needle, for example, to an injection port, a Y-site and the like. In those cases, the needle assembly is provided with an internally threaded piggy back connector 40 which is movably mounted on the tube 13 for coupling with a member receiving the needle in the retracted position of the sheath 17.

As indicated in FIG. 17, a second line is formed of a tube 41, for example, of plastic having an external thread 42 at one end and a septum 43 sealing off the end of the tube 41. After piercing of the septum 43 by the needle 15 of the needle assembly 10, the connector 40 is slid along the tube 13 to abut a flange or collar 15 on the end of the tube 13 and threaded onto the external thread 42 of the second line. In this respect, the connector 40 is provided with an internal thread 40'. Alternatively, any other type of coupling means may be used to couple the needle assembly 10 to the tube 41.

Referring to FIG. 18, in still another embodiment, the needle assembly may employ a syringe 44 having a barrel 45, a plunger 46 slidably mounted in the barrel 45 and a needle 47 which extends from the barrel 45. In this embodiment, the sheath 17 is telescopically mounted on the barrel 45 in a retrofit manner with one end extending beyond the needle 17 in protected relation. As above, the sheath is movable longitudinally of the needle 47 and the barrel 45 between the extended position (not shown) covering over the needle 47 and a retracted position, as shown, exposing the needle 47.

As above, a projection or pin 21 is provided on the barrel 45 while a guide slot 22 is provided in the sheath 17. As indicated, the rear face of the sheath 17 is constructed so that a flange 48 is formed thereon. In this embodiment, there is no resilient means for biasing the sheath 17 into the extended position. Instead, after filling of the syringe 44 in a normal manner while using the sheath 17 to prevent any potential cutting, a nurse or other technician would locate and otherwise prepare the site for injection. At this time, the "Dart" method of inserting the needle would be used. By this is meant that the nurse would hold the needle syringe by the barrel 45 in a manner similar to holding a dart. The nurse would then determine how deep the needle 47 is to penetrate into the skin of the patient. This depth would be based upon experience, the anatomy of the patient and the like. The nurse would then jab the skin and continue to exert pressure until the desired depth is achieved. The quicker and more uniform the movement of the needle 47, the less trauma that is to be expected. When the needle 47 is preattached to the syringe 44, the nurse can predetermine how deep the skin is to be penetrated. Thus, the nurse or user may position his/her fingers, as indicated in FIG. 18, at the location which corresponds to the depth desired for the particular patient. When the needle 47 reaches the predetermined depth, the flange 48 butts up against the fingers thereby alerting the user to the fact that the proper depth has been reached and the needle cannot go any further without the user moving his/her fingers. By using this technique, penetration time is minimized. The concern for going too deep is also eliminated, the exact penetration depth desired is achieved and the skill required to perform the procedure is substantially reduced.

After implantation of the needle 47, the user may then use an index finger to depress the plunger 46 into the barrel 45 in order to inject medicament from the barrel 45 through the needle 47 into the muscle of the patient. Thereafter, the syringe 44 is withdrawn from the patient so that the needle 47 is drawn from the muscle. In this respect, if no resilient means is provided between the sheath 17 and the syringe barrel 45, the sheath may be manually extended so as to encase the needle 47. Alternatively, a resilient means may be provided between the sheath 17 and the barrel 45 in a manner as described above so that the sheath 17 is biased under a biasing force into the extended position.

Figure 20:
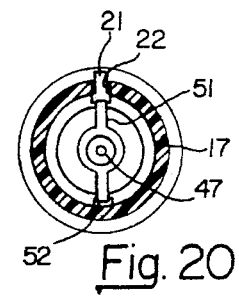
FIG. 20 illustrates a view taken on line 20—20 of FIG. 19.
Figure 21:
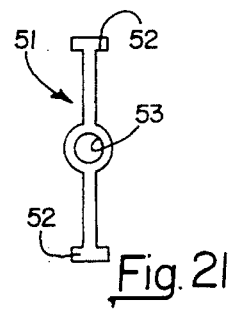
FIG. 21 illustrates a view of a rubber strip employed in the assembly of FIG. 18.
Figure 19:
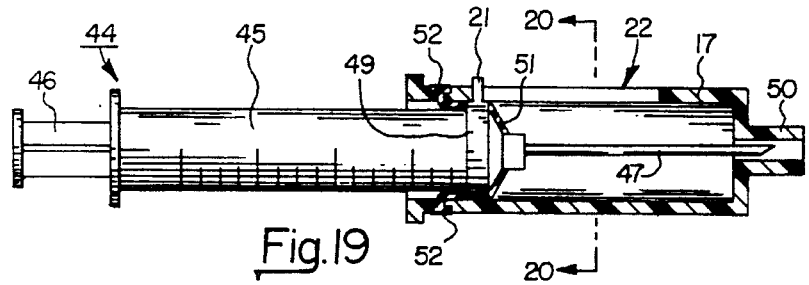
FIG. 19 illustrates a part cross-sectional view of a protected sheath mounted on a syringe in accordance with the invention.

Referring to FIGS. 19 to 21, wherein like reference characters indicate like parts as above, the syringe 44 may also be made integral with the sheath 17. In this respect, a retainer ring 49 is secured to the barrel 45 and has a projection 21 extending outwardly thereof radially of the barrel 45. This projection 21 slides within the guide slot 22 of the sheath 17. In addition, the sheath 17 may be provided with a reduced distal end 50 for passage of the needle 47. As indicated, the tip of the needle 47 would be positioned within the reduced distal end 50 of the sheath 17 when the sheath 17 is in the extended position.

In this embodiment, a resilient means 51 is provided for biasing the sheath 17 from the retracted position to the extended position (as shown). In this respect, the resilient means 51 is in the form of a rubber strip (see FIG. 21) which is secured at each end 52 in diametrically disposed parts or slots in the sheath 17. In addition, the rubber strip 51 has a centrally disposed aperture 53 to allow passage of the needle 47 while at the same time allowing a central portion of the rubber strip 51 to engage against the end of the barrel 45 of the syringe 44.

When the sheath 17 is moved to the retracted position, the rubber strip 51 elongates, thereby imparting a forwarding bias on the sheath 17.

Figure 22:
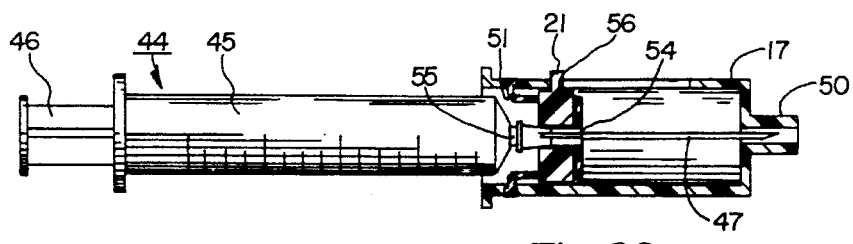
FIG. 22 illustrates a modified mounting arrangement of a protective sheath on a syringe in accordance with the invention.

Referring to FIG. 22, wherein like reference characters indicate like parts as above, the needle 47 may be mounted on a hub 54 which, in turn, is mounted on a nose 55 of the barrel 45 of the syringe 44. In this case, a retainer ring 56 may be mounted on the hub 54 with an integral projection 21 thereon sliding in the slot 22 of the sheath 17. In this case, the rubber strip 51 is secured at the ends to the sheath 17 while having the apertured central portion disposed on the needle hub 54. Suitable slots are provided in the retainer ring 56 to allow passage of the rubber strip 51 therethrough.

Figure 23:
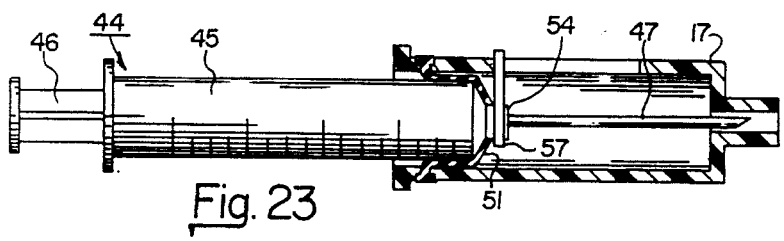
FIG. 23 illustrates a modified arrangement of a sheath mounted on a syringe in accordance with the invention.

Alternatively, as shown in FIG. 23, wherein like reference characters indicate like parts as above, a bracket 57 on which the projection 21 is mounted on the needle hub 54 in front of the rubber strip 51 relative to the syringe barrel 45 so as to facilitate assembly of the sheath 17 on the syringe 44.

Figure 24:
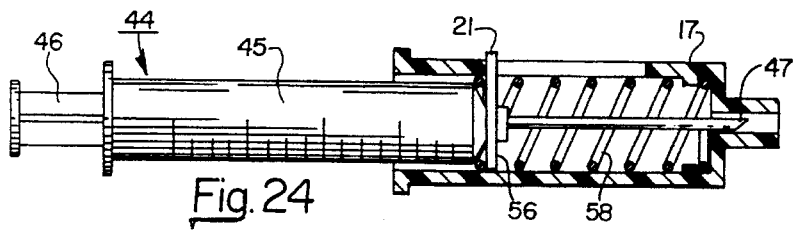
FIG. 24 illustrates a further modified arrangement of a sheath mounted on a syringe and employing a spring with the sheath.

Referring to FIG. 24, wherein like reference characters indicate like parts as above, the resilient means within the sheath 17 may be in the form of a coiled spring 58 which is disposed within the sheath 17 and which abuts the barrel 45 at one end and the distal end of the sheath 17 at the opposite end.

Figure 25:
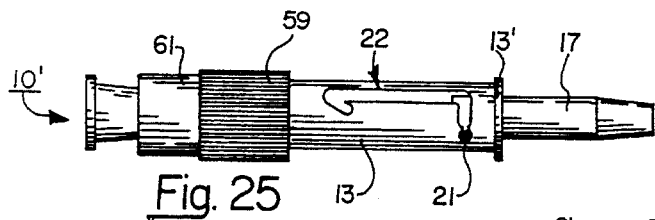
FIG. 25 illustrates a further embodiment of a protected needle assembly having multiple uses.
Figure 27:
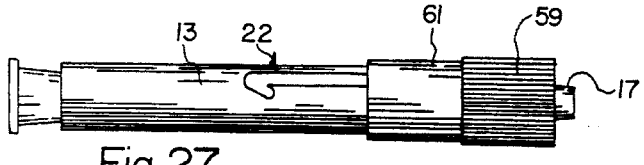
FIG. 27 illustrates the needle assembly of FIG. 25 in a condition for a different use in accordance with the invention.
Figure 28:
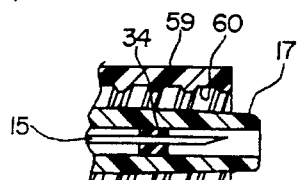
FIG. 28 illustrates a part cross-sectional view of the distal end of the needle assembly of FIG. 27.

Referring to FIG. 25, wherein like reference characters indicate like parts as above, the protected needle assembly 10' may be constructed as an universal assembly for multiple uses. As indicated, the needle assembly 10' is provided with an annular connector 59 similar to the connector 40 as described above with respect to the embodiment of FIG. 17. This connector 59 is slidably mounted on the tube 13 so as to move from a retracted position as shown in FIG. 25 to an extended position as shown in FIG. 27. The connector is provided with an internal thread 60 as indicated in FIG. 28 so as to form a male luer connector with the distal end of the sheath 17. The connector 59 is further integrally connected to an annular sleeve or collar 61 which allows the connector 59 to be projected beyond the flange 13' of the rigid tube 13 into the extended position of FIG. 27. In addition, this collar 61 is provided with a suitable annular shoulder or stop or the like to abut against the flange 13 on the rigid tube 13 to arrest the movement of the collar 59 to the extended position shown in FIG. 27.

As shown in FIG. 25, the sheath 17 is in the extended position while the connector 59 is in a retracted position. In addition, the sheath 17 is open-ended, that is, there is no septum closing off the sheath 17. Also, the projection 21 is disposed in the constricted portion 27 adjacent the guide slot 22 so as to securely lock the sheath 17 in the extended position.

Figure 26:
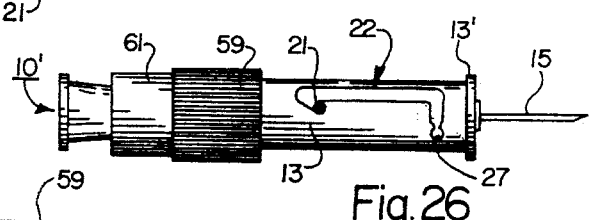
FIG. 26 illustrates a view of the needle assembly of FIG. 25 in a condition with the protective sheath in a retracted position.

Referring to FIG. 26, after the projection 21 is moved out of the constricted portion 27, the needle assembly of FIG. 25 may be used in a fashion as above wherein the sheath 17 is butted against a septum while the needle assembly 10' is pressed forwardly. In this way, the sheath 17 is retracted into the tube 13 and the projection 21 is moved into the V-shaped slot portion at the rear of the guide slot 22 to hold the sheath 17 in the retracted position. At this time, the needle 15 is exposed. In this manner, the needle assembly 10' is used also for piercing parenteral vials, Y-sites, rubber septums in IV bags and injection ports.

Referring to FIG. 27, in another condition of use, with the projection 21 in the constricted portion 27 so that the sheath 17 is locked in place, the connector 59 is slid forwardly to have the collar 61 abut the flange 13' on the tube 13 with the connector 59 disposed concentrically and coaxially over the sheath 17. As indicated in FIG. 28, in this condition, the connector 59 forms a male luer connector. As in the embodiment of FIG. 10, a washer 34 seals the needle 17 relative to the sheath 17 so that fluid is prevented from leaking out of the needle assembly.

As indicated in FIG. 27, the collar 61 covers over the forward end of the guide slot 22. In this respect, the collar 61 may be provided with a suitable slot or other means to engage the projection 21 and prevent movement of the sheath 17.

Figure 29:
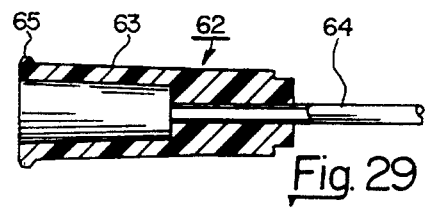
FIG. 29 illustrates a part cross-sectional view of a needle hub unit for employment with the connector of FIG. 27.
Figure 30:
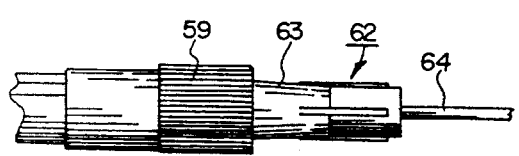
FIG. 30 illustrates a partial view of the needle hub of FIG. 29 mounted on the connector of FIG. 27 in accordance with the invention.

Referring to FIGS. 27, 29 and 30, a needle assembly 62 employing a hub 63 and a needle 64 which extends from the hub 63 can be mounted on the needle assembly 10'. As indicated, the hub 63 has a conical exterior and a conical interior. In addition, the hub 63 has a pair of ears 65 (or an annular flange) which permits threading of the hub 63 into the internally threaded connector 59 as indicated in FIG. 30. In the condition indicated in FIG. 30, the needle assembly 62 may be used for piercing a suitable septum to deliver fluid thereto or to remove fluid therefrom.

Figure 31:
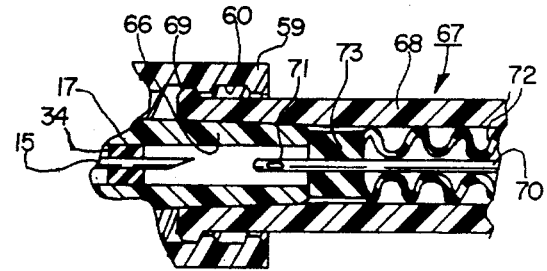
FIG. 31 illustrates a cross-sectional view of the distal end of the connector of FIG. 27 in a further condition of use with a septum luer in accordance with the invention.

Referring to FIG. 31, wherein like reference characters indicate like parts as above, in another condition of use the needle assembly 10' may be provided with a conical hub 66 which is threaded into the connector 59 to abut the end of the sheath 17. In this embodiment, the connector 59 (shown partially) may be used to connect to a septum luer connector 67 where needles are not to be used. As indicated, the septum luer connector 67 has a tubular member 68 formed with an external thread 69 to thread into the connector 59, a needle 70 having a closed rounded end with an eyelet or aperture 71 in the side wall and a collapsible sleeve 72 which carries a septum 73 at the end for sealing off the needle 70 to the outside environment about the tubular member 68. Prior to use, the collapsible sleeve 72 is in an uncollapsed state so that the septum 73 is spaced in front of the rounded end of the needle 70 or is shaped as described in copending patent application Ser. No. 08/328,045, filed Oct. 24, 1994 to receive the closed end of the needle 70 with an interference fit.

In use, the needle assembly 10' is brought into alignment with the septum luer connector 67 and the connector 59 is then threaded onto the external thread 69 of the tubular member 68. At this time, the hub 66 which functions as a male adapter, pushes against the septum 73 of the septum luer connector 67 so as to push the septum 73 over the needle 70 while collapsing the sleeve 70. Typically, the septum 73 has a slit to enhance passage of the needle 70. The amount of penetration of the hub 66 is sufficient to expose the eyelet 71 in order to communicate the needle 70 with the needle 15. Alternatively, the hub 66 may first penetrate the luer connector 67 and then the connector 59 may be threaded onto the tubular member 68.

Referring to FIG. 25, the needle assembly 10' may also be used in a condition wherein the sheath 17 is locked relative to the tube 13, for example, by having the projection 21 located in the constricted portion 27. In this embodiment, distal end of the sheath 17 would be tapered so as to form a male luer. In this condition of use, a needle assembly 62 as shown in FIG. 29 may be slidably mounted on the distal end of the sheath 17 to form a slip connection, that is, a frictional locking between the tapered end of the sheath 17 and the conical interior of the hub 63. Alternatively, a female luer connector may be slip fit onto the tapered end of the sheath 17 to form a connection. Such a slip fit connection would be an alternative to the male luer lock connection as provided by the internally threaded connector 59 shown in FIG. 28. Such a connector 59 provides a positive lock as the connector 59 has to be rotated to unlock from a hub 62 or a connector 67 such as shown in FIG. 31 or the like.

Alternatively, any suitable type of lock may be used instead of the internally threaded connector 59. For example, one or more grippers may be secured to the needle assembly to engage with a collar or the like on a connector assembly mated with the needle assembly. In this respect, the grippers may be snapped onto the needle assembly when the use of the grippers is required. In this case, the grippers may be used to cover over the guide slot 22 in order to prevent the projection 21 from moving along the guide slot. Alternatively, the grippers may be positioned to allow the projection 21 to move into the V-shaped portion of the guide slot so as to expose the needle for penetration into the attached connector, an injection port containing a septum.

By using a threaded connector 59 as described above but of a different thread type, the needle assembly can be secured with the sheath partially and retracted to another connector with the needle piercing the septum. This is in addition to locking the sheath in place and obtaining a standard luer lock connection.

Other improvements which may be used with the needle assembly include the use of a blunt needle, that is, a needle having an open end defined by a circumferential wall with a rounded cross-section at the end so as to avoid cutting or piercing of the material of the septum. Alteratively, the needle may be provided with a closed rounded end with one or more apertures in a side wall. In such embodiments, the risk of debris being created during piercing and unpiercing of the septum may be reduced.

The invention thus provides a needle assembly which protects against inadvertent needle sticks. A major advantage of the protected needle assembly is the fact that when protected by a rubber septum, there is no blood exposure upon withdrawal of a septum. Further, the protected needle assembly becomes a sterile connection device when both septums are swabbed with alcohol prior to hook-up. Typically, in these cases, both septums are slit to facilitate piercing, for example by a blunt cannula and connection between the two septums.

What is claimed is:

1. A protected needle assembly comprising a housing including a hub at a proximal end for mounting on at least one of a drug delivery system, a syringe and a blood receiving receptacle and a rigid tube;

a needle mounted on said hub and within said tube, said needle extending beyond said tube;

a sheath disposed concentrically about said needle with one end extending beyond said needle in protective relation, said sheath being movable longitudinally of said needle and said tube between an extended position covering over said needle and a retracted position exposing said needle;

at least one projection on one of said sheath and said tube;

a guide slot in the other of said sheath and said tube receiving said projection, said guide slot having a circumferentially directed portion at one end receiving said projection in said extended position of said sheath and an inclined portion at an opposite end directed toward said one end to receive and retain said projection in said retracted position; and resilient means for biasing said sheath from said retracted position to said extended position.

2. A protected needle assembly as set forth in claim 1 wherein said resilient means includes a rubber sleeve secured to said housing at one end and having a wall at a distal end in facing relation to said needle for piercing thereby.

3. A protected needle assembly as set forth in claim 1 wherein said circumferentially directed portion has a cam-shaped surface for directing said projection from said longitudinally directed portion circumferentially into said circumferentially directed portion when said sheath is biased into said extended position.

4. A protected needle assembly as set forth in claim 3 wherein said guide slot has an inclined portion at said one end extending from said longitudinally directed portion opposite to said circumferentially directed portion to receive said projection prior to movement of said projection relative to and along said longitudinally directed portion.

5. A protected needle assembly as set forth in claim 1 which further comprises a constricted portion adjacent an end of said circumferentially directed portion for receiving said projection in a permanently locked relation for disposal purposes.

6. A protected needle assembly as set forth in claim 1 which further comprises a rubber septum on one end of said sheath for sealing said needle therein, said septum having a slit valve therein.

7. A protected needle assembly as set forth in claim 1 which further comprises an air filter mounted in said sheath to permit filtered air to enter into said sheath.

8. A protected needle assembly as set forth in claim 1 wherein said sheath is made of a clear plastic to allow visual inspection of said needle.

9. A protected needle assembly as set forth in claim 1 which further comprises a cap mounted at one end of said sheath to seal said needle therein, said cap having a slit therein to facilitate passage of said needle therethrough.

10. A protected needle assembly as set forth in claim 9 wherein said cap has a hemi-spherical tip.

11. A protected needle assembly as set forth in claim 9 which further comprises a washer sealingly mounted in said sheath with said needle passing therethrough in slidably sealed relation, said washer being disposed near a distal end of said needle.

12. A protected needle assembly as set forth in claim 1 wherein said sheath has a surface on a distal end for frictionally engaging a surface to be pierced with said needle.

13. A protected needle assembly as set forth in claim 12 wherein said surface of said sheath is roughened.

14. A protected needle assembly as set forth in claim 1 wherein said projection has a manually engagable portion extending radially of said tube.

15. A protected needle assembly as set forth in claim 1 wherein said sheath in telescopically mounted over said tube and which further comprises a stop movably mounted on said tube for arresting movement of said sheath along said tube into a predetermined retracted position.

16. A protected needle assembly as set forth in claim 1 wherein said guide slot has at least one angularly disposed portion positioned intermediately of said longitudinally disposed portion to receive said projection therein to limit the length of exposure of said needle from said sheath.

17. A protected needle assembly as set forth in claim 1 which further comprises a connector movably mounted on said tube for coupling with a member receiving said needle in said retracted position of said sheath.

18. A protected needle assembly as set forth in claim 1 wherein said sheath is telescopically mounted within said tube with said projection on said sheath and said slot in said tube.

19. A protected needle assembly a set forth in claim 1 which further comprises a rubber septum at one end of said sheath for sealing said needle therein and a collapsible sleeve integral with said septum and abutting said hub at one end to permit twisting of said sheath relative to said tube to impart a bias on said sheath in a circumferential direction.

* * * * *